US012544095B2

(12) United States Patent
Akagane

(10) Patent No.: US 12,544,095 B2
(45) Date of Patent: Feb. 10, 2026

(54) ULTRASONIC TREATMENT TOOL, VIBRATION TRANSMISSION MEMBER, AND METHOD OF MANUFACTURING VIBRATION TRANSMISSION MEMBER

(71) Applicant: OLYMPUS MEDICAL SYSTEMS CORP., Tokyo (JP)

(72) Inventor: Tsunetaka Akagane, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 389 days.

(21) Appl. No.: 18/109,615

(22) Filed: Feb. 14, 2023

(65) Prior Publication Data

US 2023/0255656 A1 Aug. 17, 2023

Related U.S. Application Data

(60) Provisional application No. 63/311,115, filed on Feb. 17, 2022.

(51) Int. Cl.
*A61B 17/32* (2006.01)

(52) U.S. Cl.
CPC ................. *A61B 17/320092* (2013.01); *A61B 2017/320094* (2017.08)

(58) Field of Classification Search
CPC .......... A61B 2017/320094; A61B 17/320092; A61B 17/320068; A61B 2017/320069; A61B 2017/320072; A61B 2017/320073; A61B 2017/320074; A61B 2017/320075; A61B 2017/320077; A61B 2017/320078; A61B 2017/320082; A61B 2017/320093; A61B 2017/320095; A61B 18/14; A61B 18/1445; A61B 2017/22008; A61B 2017/22007; A61B 2017/2825; A61B 2017/320089; A61B 2018/00994
See application file for complete search history.

(56) References Cited

U.S. PATENT DOCUMENTS

2009/0216157 A1* 8/2009 Yamada ......... A61B 17/320092
601/2

FOREIGN PATENT DOCUMENTS

JP 2011-139912 A 7/2011

* cited by examiner

*Primary Examiner* — Katherine M Shi
(74) *Attorney, Agent, or Firm* — Morgan, Lewis & Bockius LLP

(57) ABSTRACT

An ultrasonic treatment tool comprises: a blade including a treatment portion, the treatment portion is configured to treat a treatment target and the blade is configured to transmit an ultrasonic vibration to the treatment portion, a pattern on at least part of an outer surface of the treatment portion, the pattern including a plurality of protrusions, each protrusion includes at least one side surface intersecting with a vibration direction of the ultrasonic vibration, the at least one side surface defining a cavitation surface, at least one cavitation surface is located within a pitch width in the vibration direction, an amplitude of the ultrasonic vibration defines the pitch width.

17 Claims, 7 Drawing Sheets

ULTRASONIC TREATMENT TOOL, VIBRATION TRANSMISSION MEMBER, AND METHOD OF MANUFACTURING VIBRATION TRANSMISSION MEMBER

CROSS-REFERENCE TO RELATED APPLICATION

This application is based on and claims priority under 35 U.S.C. § 119 to U.S. Provisional Application No. 63/311,115, filed Feb. 17, 2022, the entire contents of which are incorporated herein by reference.

BACKGROUND

1. Technical Field

The present disclosure relates to an ultrasonic treatment tool, a vibration transmission member, and a method of manufacturing the vibration transmission member.

2. Related Art

An ultrasonic treatment tool, which is for treatment of a region to be treated (hereinafter, referred to as a treatment target) in body tissue by application of ultrasonic energy, has been known conventionally (see, for example, Japanese Patent Application Laid-open No. 2011-139912).

The ultrasonic treatment tool described in Japanese Patent Application Laid-open No. 2011-139912 grasps the treatment target between a vibration transmission member that transmits ultrasonic vibration and a jaw that is opened and closed relatively to the vibration transmission member. The treatment target is treated by application of the ultrasonic vibration to the treatment target from a distal end portion (hereinafter, referred to as a treatment portion) of the vibration transmission member of the ultrasonic treatment tool.

To treat the treatment target by use of both cavitation and frictional heat, a cavitation causing portion is provided in the treatment portion of the ultrasonic treatment tool described in Japanese Patent Application Laid-open No. 2011-139912.

Specifically, the cavitation causing portion is a portion that has an uneven shape with intersecting surfaces intersecting a vibration direction of the ultrasonic vibration.

SUMMARY

In some embodiments, an ultrasonic treatment tool comprises: a blade including a treatment portion, the treatment portion is configured to treat a treatment target and the blade is configured to transmit an ultrasonic vibration to the treatment portion, a pattern on at least part of an outer surface of the treatment portion, the pattern including a plurality of protrusions, each protrusion includes at least one side surface intersecting with a vibration direction of the ultrasonic vibration, the at least one side surface defining a cavitation surface, at least one cavitation surface is located within a pitch width in the vibration direction, an amplitude of the ultrasonic vibration defines the pitch width.

In some embodiments, provided is a blade comprising: a treatment portion configured to treat a treatment target, wherein the blade is configured to transmit an ultrasonic vibration to the treatment portion, a pattern on at least part of an outer surface of the treatment portion, the pattern including a plurality of protrusions, wherein each protrusion includes at least one side surface intersecting with a vibration direction of the ultrasonic vibration and the at least one side surface defining a cavitation surface, at least one cavitation surface is located within a pitch width in the vibration direction, wherein an amplitude of the ultrasonic vibration defines the pitch width, the pattern including the plurality of protrusions extends in the vibration direction a distance that is a multiple of the pitch width.

In some embodiments, provided is a method of manufacturing a vibration transmission member. The method comprises: forming by laser processing a pattern on at least part of an outer surface of a treatment portion of a blade, the pattern including a plurality of protrusions, each protrusion includes at least one side surface intersecting with a vibration direction of an ultrasonic vibration transmitted along the treatment portion and the at least one side surface defining a cavitation surface, at least one cavitation surface is located within a pitch width in the vibration direction, an amplitude of the ultrasonic vibration defines the pitch width, and the pattern including the plurality of protrusions extends in the vibration direction a distance that is a multiple of the pitch width.

The above and other features, advantages and technical and industrial significance of this disclosure will be better understood by reading the following detailed description of embodiments of the disclosure, when considered in connection with the accompanying drawings.

DETAILED DESCRIPTION

Modes for implementing the disclosure (hereinafter, embodiments) will be described hereinafter while reference is made to the drawings. The disclosure is not limited by the embodiments described hereinafter. Furthermore, any portions that are the same will be assigned with the same reference sign, throughout the drawings.

Schematic Configuration of Treatment System

Figure 1:
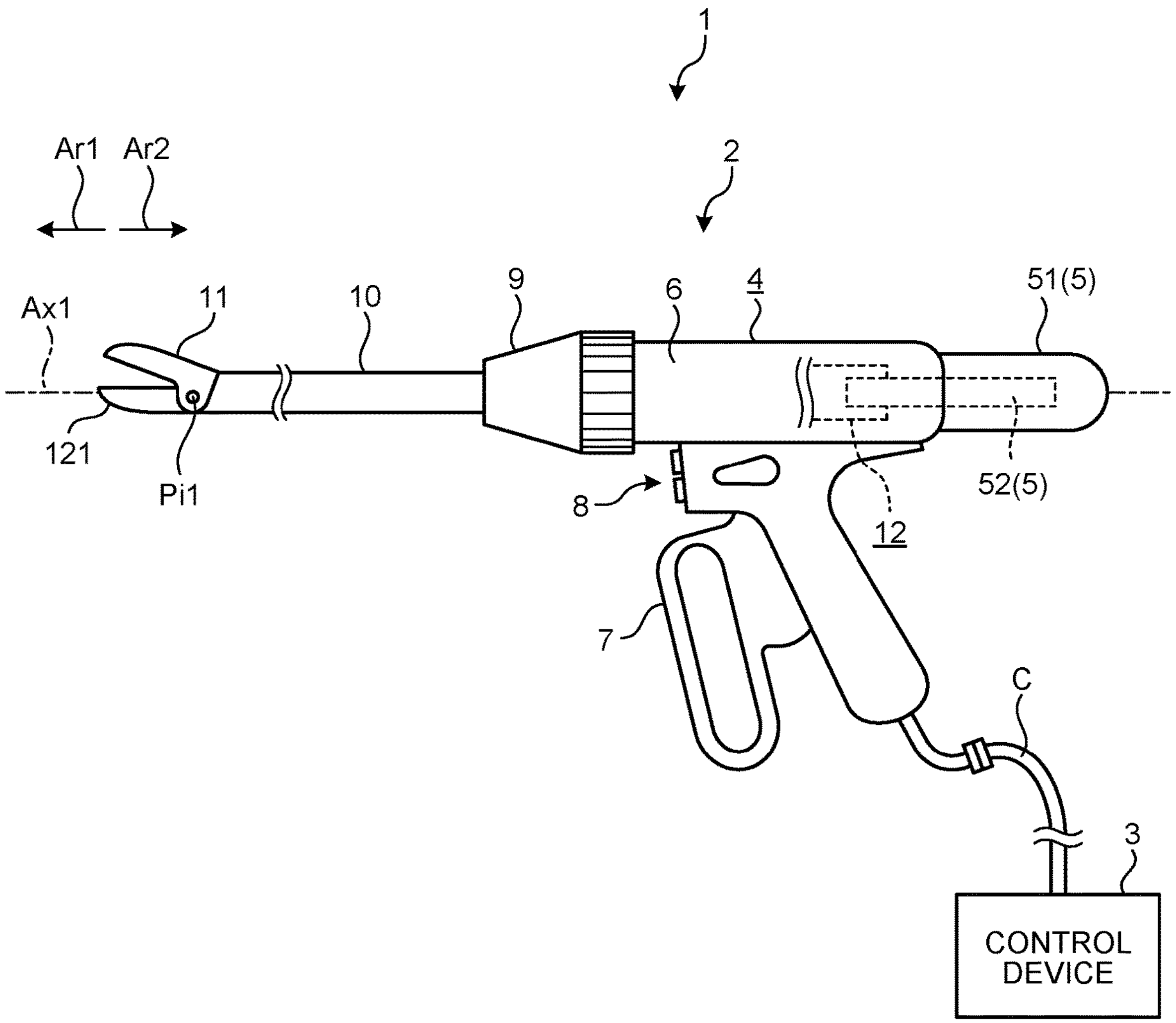
FIG. 1 is a diagram illustrating a treatment system according to an embodiment.

FIG. 1 is a diagram illustrating a treatment system 1 according to an embodiment.

The treatment system 1 is for treatment of a part to be treated in body tissue (hereinafter, referred to as a treatment target) by application of treatment energy to the treatment target. The treatment energy in this embodiment is ultrasonic energy and high frequency energy. Furthermore, treatment that is able to be executed by the treatment system 1 according to the embodiment is, for example, coagulation (sealing) of the treatment target or incision of the treatment target. Furthermore, the coagulation and the incision may be performed at the same time. This treatment system 1 includes, as illustrated in FIG. 1, an ultrasonic treatment tool 2 and a control device 3.

Configuration of Ultrasonic Treatment Tool

Hereinafter, one of directions along a central axis Ax1 (FIG. 1) of a sheath 10 will be referred to as a distal direction Ar1 and the other direction will be referred to as a proximal direction Ar2. Furthermore, a "width direction" referred to hereinafter means a direction orthogonal to the central axis Ax1 and an opening and closing direction along which a jaw 11 is opened and closed relatively to a treatment portion 121, the direction being orthogonal to the plane of paper of FIG. 2 and lateral in FIG. 3.

Figure 2:
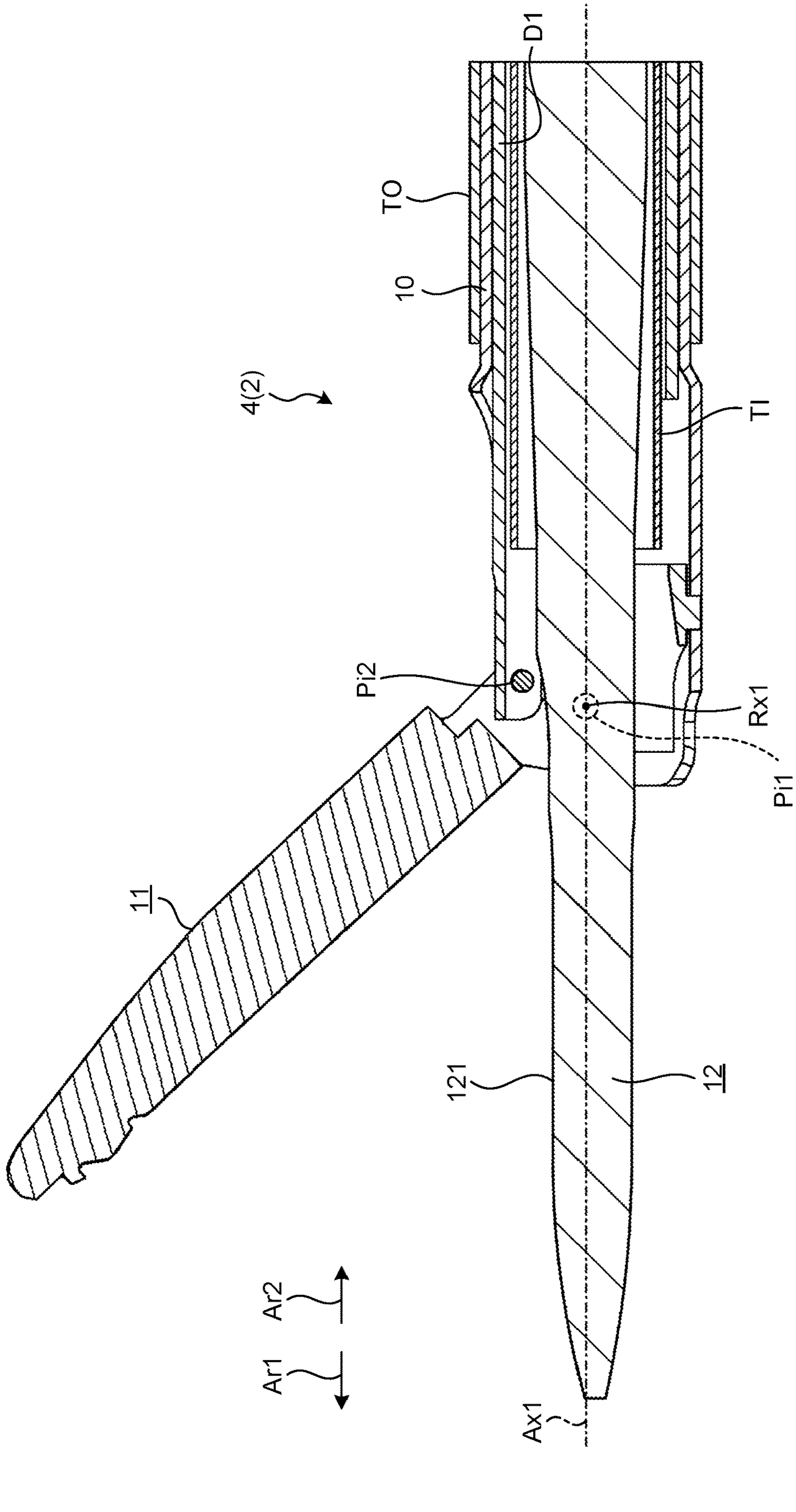
FIG. 2 is a diagram illustrating a configuration of a distal end portion of an ultrasonic treatment tool.
Figure 3:
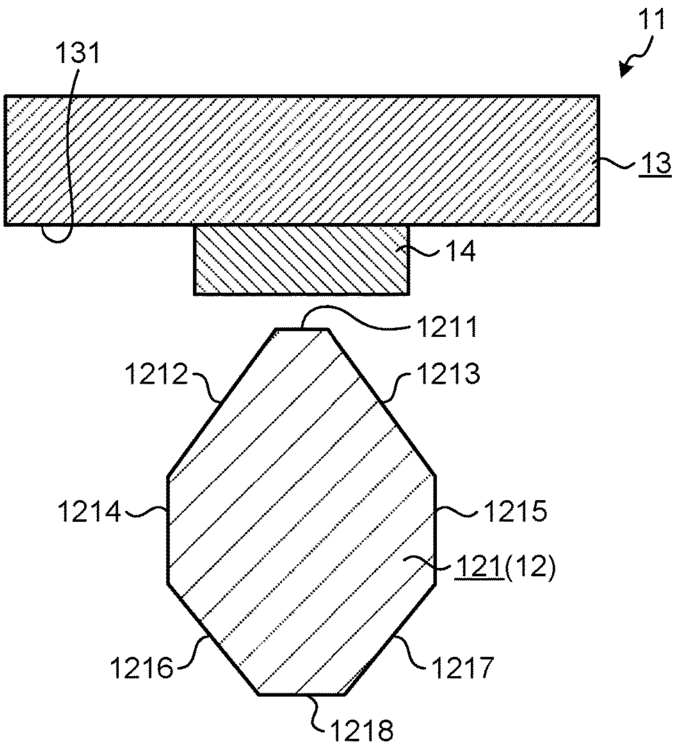
FIG. 3 is a diagram illustrating the configuration of the distal end portion of the ultrasonic treatment tool.

FIG. 2 and FIG. 3 are diagrams illustrating a configuration of a distal end portion of the ultrasonic treatment tool 2. Specifically, FIG. 2 is a sectional view of the distal end portion of the ultrasonic treatment tool 2, the distal end portion being cut along a plane including the central axis Ax1 of the sheath 10 in a state where the jaw 11 and a vibration transmission member 12 (blade) are included in the plane. FIG. 3 is a sectional view of the distal end portion of the ultrasonic treatment tool 2, the distal end portion being cut along a plane orthogonal to the central axis Ax1.

The ultrasonic treatment tool 2 is a treatment tool for treatment of a treatment target by application of ultrasonic energy and high frequency energy to the treatment target. This ultrasonic treatment tool 2 includes, as illustrated in FIG. 1, a handpiece 4 and an ultrasonic transducer unit 5.

The handpiece 4 includes, as illustrated in FIG. 1 to FIG. 3, a holding case 6 (FIG. 1), an operation handle 7 (FIG. 1), switches 8 (FIG. 1), a rotation knob 9 (FIG. 1), the sheath 10 (FIG. 1 and FIG. 2), the jaw 11, and the vibration transmission member 12.

The holding case 6 supports the whole ultrasonic treatment tool 2.

The operation handle 7 is attached movably in relation to the holding case 6 and receives an opening operation or a closing operation from an operator, such as an operating surgeon.

The switches 8 are provided in a state of being exposed to the exterior of the holding case 6 and receives treatment operations from an operator, such as an operating surgeon.

The rotation knob 9 has an approximately cylindrical shape coaxial with the central axis Ax1 and is provided near an end of the holding case 6, the end being in the distal direction Ar1. The rotation knob 9 receives a rotating operation from an operator, such as an operating surgeon. The rotating operation causes the rotation knob 9 to rotate about the central axis Ax1, relatively to the holding case 6. Furthermore, rotation of the rotation knob 9 causes the sheath 10, the jaw 11, and the vibration transmission member 12 to rotate about the central axis Ax1.

The sheath 10 is a cylindrical pipe formed of an electrically conducting material, such as metal.

A first pin Pi1 (FIG. 1 and FIG. 2) that extends in a direction orthogonal to the plane of paper of FIG. 1 and supports the jaw 11 rotatably about a first rotation axis Rx1 (FIG. 2) is fixed to an end portion of the sheath 10, the end portion being in the distal direction Ar1.

An outer peripheral surface of the sheath 10 is covered with an electrically insulating outer tube TO (FIG. 2). Furthermore, an inner peripheral surface of the sheath 10 is covered with an electrically insulating inner tube TI (FIG. 2).

Part of the jaw 11 is formed of an electrically conducting material. This jaw 11 is configured to be rotatable about the first rotation axis Rx1 relatively to the sheath 10, by being supported about the first pin Pi1 at the end portion of the sheath 10, the end portion being in the distal direction Ar1, as described above. In association with movement of an opening and closing mechanism D1 (FIG. 2) in the distal direction Ar1 or proximal direction Ar2 according to an opening or closing operation on the operation handle 7 by an operator, such as an operating surgeon, the jaw 11 is opened or closed relatively to the end portion 121 (hereinafter, referred to as the treatment portion 121) of the vibration transmission member 12, the end portion 121 being in the distal direction. That is, the jaw 11 is capable of grasping a treatment target between the jaw 11 and the treatment portion 121.

The jaw 11 includes, as illustrated in FIG. 3, an arm 13 and a pad 14.

The arm 13 is formed of an electrically conducting material and is an elongated member extending along the central axis Ax1.

The first pin Pi1 is inserted through an end portion of this arm 13, the end portion being in the proximal direction Ar2. The arm 13 is supported rotatably about the first rotation axis Rx1 at the sheath 10.

Furthermore, a second pin Pi2 (FIG. 2) fixed to an end portion of the opening and closing mechanism D1, the end portion being in the distal direction Ar1, is inserted through an end portion of the arm 13, the end portion being in the proximal direction Ar2. The arm 13 is thereby connected to the opening and closing mechanism D1. In association with movement of the opening and closing mechanism D1 in the distal direction Ar1 or proximal direction Ar2 according to an opening or closing operation on the operation handle 7 by an operator, such as an operating surgeon, the arm 13 rotates about the first rotation axis Rx1.

The pad 14 is formed of a resin material that is electrically insulating and biocompatible, for example, polytetrafluoroethylene (PTFE), and has an approximate rectangular parallelepiped shape extending along a longitudinal direction of the arm 13. This pad 14 is fixed to a surface 131 of the arm 13, as illustrated in FIG. 3, the surface 131 being toward the treatment portion 121. A method of fixing the pad 14 to the arm 13 may be, for example: a fixing method where mechanical fixing is achieved by protrusion of claw portions from the surface 131 of the arm 13, the surface being toward the treatment portion 121, and engagement of the claw portions with the pad 14; or insert molding.

The pad 14 comes into contact with the treatment portion 121 when the jaw 11 is brought close to the treatment portion 121.

The vibration transmission member 12 is formed of an electrically conducting material and has an elongated shape extending linearly along the central axis Ax1. Furthermore, the vibration transmission member 12 is inserted in the sheath 10 in a state where the treatment portion 121 protrudes outside the sheath 10, as illustrated in FIG. 2. In this insertion, an end portion of the vibration transmission member 12, the end portion being in the proximal direction Ar2, is mechanically connected to an ultrasonic transducer 52 included in the ultrasonic transducer unit 5, as illustrated in FIG. 1. The vibration transmission member 12 transmits ultrasonic vibration generated by the ultrasonic transducer unit 5 from the end portion of the vibration transmission member 12 to the treatment portion 121, the end portion being in the proximal direction Ar2. In this embodiment, the ultrasonic vibration is longitudinal vibration that is vibration along the central axis Ax1.

In this embodiment, the treatment portion 121 has, as illustrated in FIG. 3, an approximately octagon-shaped cross section cut upon a plane orthogonal to the central axis Ax1. The octagon shape of the cross section of the treatment portion 121 is just an example, and the cross section may have a circular shape or any other shape. For convenience of explanation, the cross section of the treatment portion 121 will be assumed to be octagon-shaped in the description hereinafter.

A surface of the treatment portion 121 will hereinafter be referred to as a first surface 1211, the surface being a surface that comes into contact with the pad 14 when the jaw 11 is brought close to the treatment portion 121. Furthermore, surfaces connected to the first surface 1211 along a circumferential direction around a central axis of the treatment portion 121 will be referred to as a second surface 1212 and a third surface 1213. Furthermore, surfaces respectively connected to the second and third surfaces 1212 and 1213 along the circumferential direction around the central axis of the treatment portion 121 will be referred to as a fourth surface 1214 and a fifth surface 1215. Furthermore, surfaces respectively connected to the fourth and fifth surfaces 1214 and 1215 along the circumferential direction around the central axis of the treatment portion 121 will be referred to as a sixth surface 1216 and a seventh surface 1217. Furthermore, a surface positioned between the sixth and seventh surfaces 1216 and 1217 and opposite to the first surface 1211 will be referred to as an eighth surface 1218.

A cavitation causing portion (pattern) 122 (see FIG. 4 and FIG. 5) is provided on at least part of an outer surface of the treatment portion 121.

A detailed configuration of the cavitation causing portion 122 will be described in a later section, "Configuration of Cavitation Causing Portion".

The ultrasonic transducer unit 5 includes, as illustrated in FIG. 1, a transducer (TD) case 51 and the ultrasonic transducer 52.

The TD case 51 supports the ultrasonic transducer 52 and is detachably connected to the holding case 6.

The ultrasonic transducer 52 generates ultrasonic vibration, under control by the control device 3. In this embodiment, the ultrasonic transducer 52 is a bolt-clamped Langevin transducer (BLT).

Configuration of Control Device

The control device 3 integrally controls operation of the ultrasonic treatment tool 2 through an electric cable C (FIG. 1).

Specifically, the control device 3 detects a treatment operation on the switches 8 by an operator, such as an operating surgeon, through the electric cable C. In a case where the control device 3 has detected the treatment operation, the control device 3 applies, through the electric cable C, treatment energy to a treatment target grasped between the jaw 11 and the treatment portion 121. That is, the control device 3 implements treatment of the treatment target.

For example, in applying ultrasonic energy to a treatment target, the control device 3 supplies drive power to the ultrasonic transducer 52 through the electric cable C. The ultrasonic transducer 52 thereby generates longitudinal vibration (ultrasonic vibration) that is vibration along the central axis Ax. Furthermore, the treatment portion 121 is vibrated at a desired amplitude by the longitudinal vibration. The ultrasonic vibration is then applied from the treatment portion 121 to the treatment target grasped between the jaw 11 and the treatment portion 121. In other words, ultrasonic energy is applied to the treatment target from the treatment portion 121.

Furthermore, for example, in applying high frequency energy to a treatment target, the control device 3 supplies high frequency power between the jaw 11 and the vibration transmission member 12 through the electric cable C. When the high frequency power is supplied between the jaw 11 and the vibration transmission member 12, high frequency current flows to the treatment target grasped between the jaw 11 and the treatment portion 121. In other words, high frequency energy is applied to the treatment target.

Configuration of Cavitation Causing Portion

A configuration of the cavitation causing portion 122 will be described next.

Figure 4:
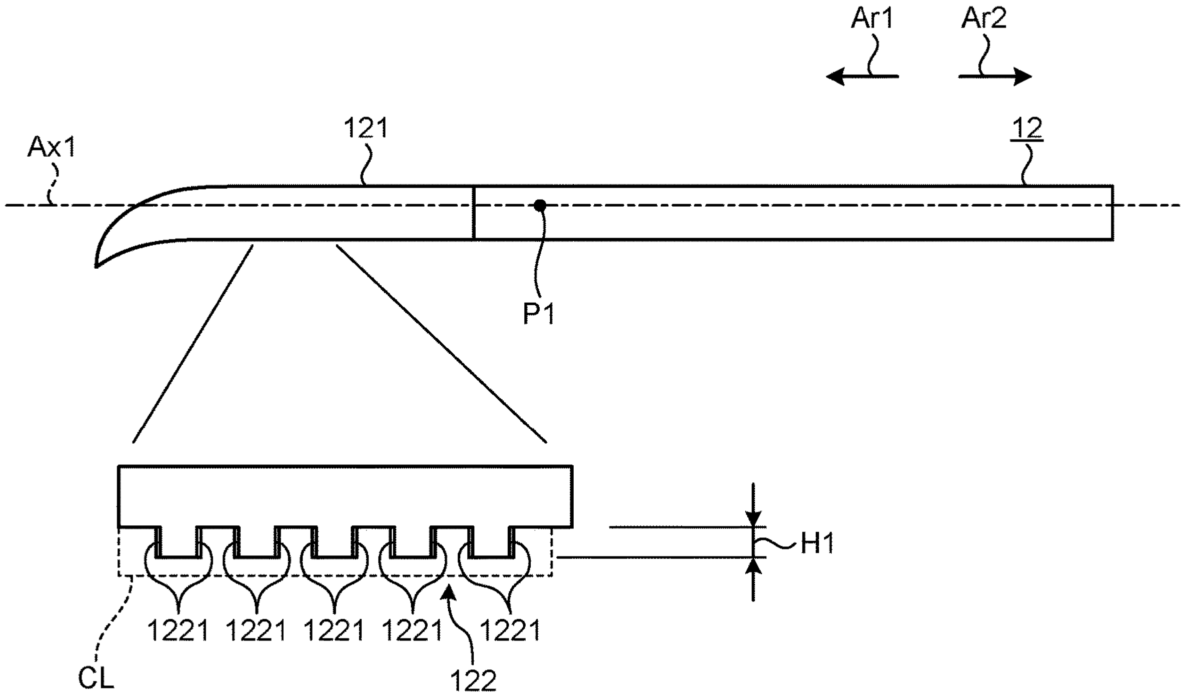
FIG. 4 is a diagram illustrating a configuration of a cavitation causing portion.
Figure 5:
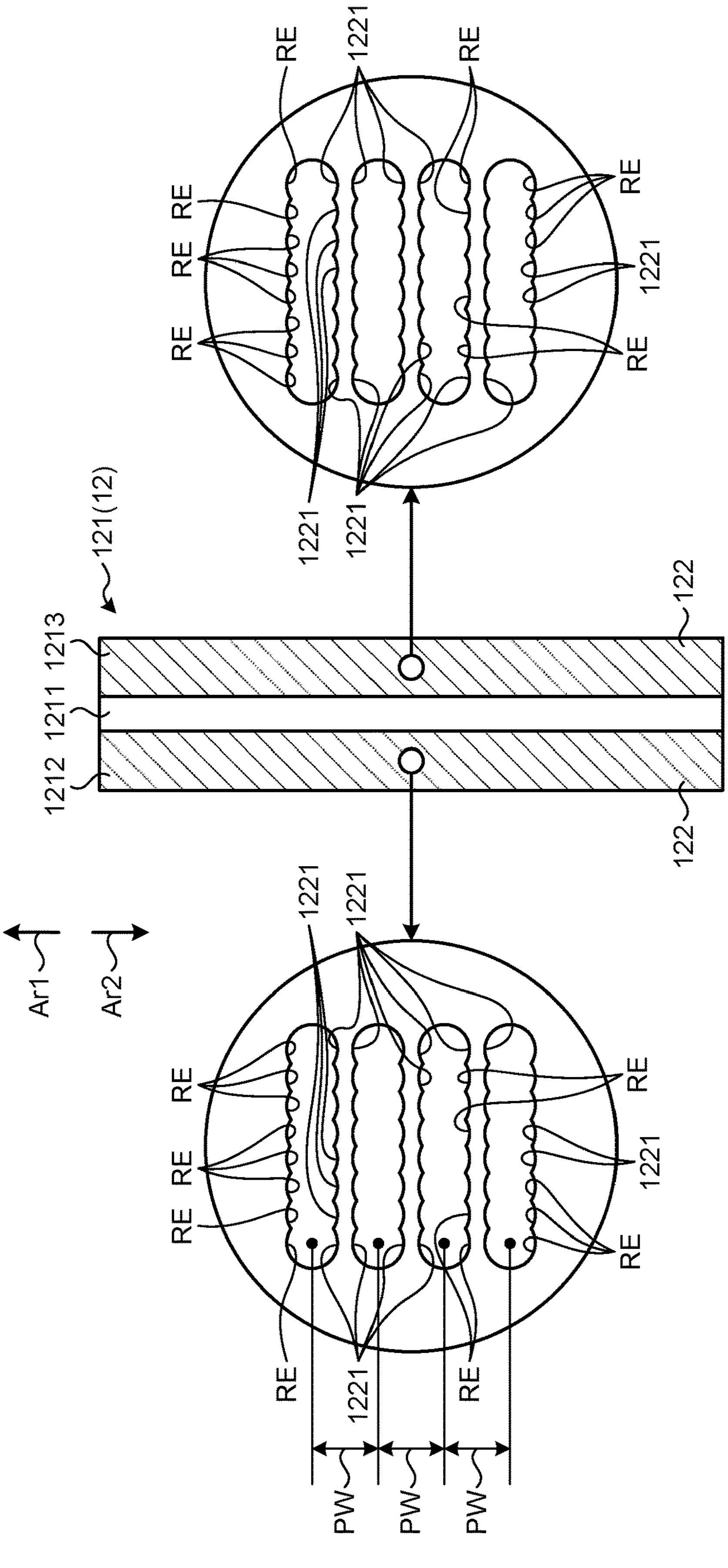
FIG. 5 is a diagram illustrating the configuration of the cavitation causing portion.

FIG. 4 and FIG. 5 are diagrams illustrating the configuration of the cavitation causing portion 122. Specifically, FIG. 4 is a diagram of the vibration transmission member 12 as viewed from a lateral direction orthogonal to the central axis Ax1. FIG. 5 is a diagram of the treatment portion 121 as viewed from the jaw 11. In FIG. 5, for convenience of explanation, a portion where the cavitation causing portion 122 is provided has been hatched.

The cavitation causing portion 122 is a portion having an uneven shape with intersecting surfaces (cavitation surface, side surface) 1221 (FIG. 4 and FIG. 5). The cavitation causing portion 122 includes a plurality of protrusions.

The plurality of protrusions includes the intersecting surfaces 1221.

The intersecting surfaces 1221 are surfaces intersecting a vibration direction of ultrasonic vibration (a longitudinal direction of the vibration transmission member 12). In this embodiment, the intersecting surfaces 1221 are surfaces orthogonal to the vibration direction of ultrasonic vibration. When these intersecting surfaces 1221 vibrate longitudinally, pressurization and depressurization are periodically repeated near the intersecting surfaces 1221. When the intersecting surfaces 1221 vibrate longitudinally in a state where the intersecting surfaces 1221 are positioned in liquid or liquid is present near the intersecting surfaces 1221, bubbles (cavities) are generated in the liquid near the intersecting surfaces 1221 due to an effect of the pressurization and depressurization. The bubbles generated disappear due to a force acting in the depressurization near the intersecting surfaces 1221. The disappearance of the bubbles generates large impact energy. The above described phenomenon is called cavitation. That is, the cavitation causing portion 122 is a portion that causes cavitation.

In this embodiment, in a case where a pitch width PW is equal to the amplitude (about 60 μm to about 100 μm) of ultrasonic vibration (FIG. 5), the intersecting surfaces 1221 are provided in a state where at least one intersecting surface 1221 (two intersecting surfaces in the example of FIG. 5) is included in the pitch width PW along the vibration direction of the ultrasonic vibration (hereinafter, referred to as a first condition). The cavitation causing portion 122 includes the plurality of protrusions extends in the vibration direction a distance that is a multiple of the pitch width PW. A distance along the vibration direction between adjacent intersecting surfaces 1221 may be equal to or smaller than the amplitude of ultrasonic vibration.

Furthermore, a height dimension H1 (FIG. 4) of the intersecting surface 1221 is set to be 30 μm or larger and 100 μm or smaller. Furthermore, as illustrated in FIG. 5, the intersecting surfaces 1221 are plurally provided in a state of being connected to each other in a direction orthogonal to the longitudinal direction of the vibration transmission member 12.

In this embodiment, as illustrated in FIG. 4, the cavitation causing portion 122 is provided at a position other than a node position P1 in ultrasonic vibration. Furthermore, as illustrated in FIG. 5, the cavitation causing portion 122 is not provided on the first and fourth to sixth surfaces 1211 and 1214 to 1216 and is provided on the second and third surfaces 1212 and 1213.

The cavitation causing portion 122 described hereinbefore is formed, as illustrated in FIG. 5, by provision of plural recessed portions (intersecting sub-surfaces) RE having a diameter of about 10 μm to about 30 μm and being circular on the second and third surfaces 1212 and 1213 by laser processing using short pulse laser. Part of side walls of the recessed portions RE functions as the intersecting surfaces 1221. In the example of FIG. 5, plural lines are juxtaposed to each other in a state of being parallel to each other along the longitudinal direction of the vibration transmission member 12, each of the plural lines being a line of a plurality of the recessed portions RE lined up in a direction orthogonal to the longitudinal direction. Furthermore, the recessed portions RE that have been lined up in the direction orthogonal to the longitudinal direction of the vibration transmission member 12 are in communication with each other. As a result, the intersecting surfaces 1221 lined up along the direction orthogonal the longitudinal direction of the vibration transmission member 12 are connected to each other. Furthermore, in the example of FIG. 5, the plural recessed portions RE are provided at predetermined intervals and are lined up but without being limited to this example, a configuration in which the plural recessed portions RE are provided randomly may be adopted instead.

The above described embodiment has the following effects.

The intersecting surfaces 1221 in the ultrasonic treatment tool 2 according to the embodiment are provided in a state of satisfying the first condition. Therefore, in treatment of a treatment target, a cavitation layer (a layer of bubbles) CL (FIG. 4) is able to be generated stably in a state of covering the whole cavitation causing portion 122. That is, the ultrasonic treatment tool 2 according to the embodiment enables both sustainment of improvement in treatment performance and prevention of sticking of tissue to the treatment portion 121.

Furthermore, the height dimension H1 of the intersecting surfaces 1221 in the ultrasonic treatment tool 2 according to the embodiment is 30 μm or larger and 100 μm or smaller.

That is, the height dimension H1 of the intersecting surfaces 1221 being 30 μm or larger enables the cavitation layer CL to be generated at the cavitation causing portion 122 upon treatment of a treatment target. Furthermore, the height dimension H1 of the intersecting surfaces 1221 being 100 μm or smaller enables the treatment portion 121 to have sufficient strength even if the cavitation causing portion 122 is provided.

Furthermore, the intersecting surfaces 1221 are plurally provided in a direction intersecting the longitudinal direction of the vibration transmission member 12 in the ultrasonic treatment tool 2 according to the embodiment.

Therefore, the cavitation causing portion 122 is able to be extended to a desired region.

In particular, the plural intersecting surfaces 1221 lined up along the direction intersecting the longitudinal direction of the vibration transmission member 12 are connected to each other. In other words, the plural recessed portions RE lined up in the direction intersecting the longitudinal direction of the vibration transmission member 12 are in communication with each other. Therefore, pieces of a treatment target that have been cut apart from each other as a result of treatment are not inhibited from moving in the direction intersecting the longitudinal direction of the vibration transmission member 12 by the side walls of the recessed portions RE and thus move smoothly in the intersecting direction. Therefore, tissue is able to be prevented from sticking to the treatment portion 121.

Furthermore, the cavitation causing portion 122 of the ultrasonic treatment tool 2 according to the embodiment is not provided in an area (first area, the first surface 1211) of the outer surface of the treatment portion 121, the area being where the pad 14 comes into contact with.

In other word, the cavitation causing portion 122 of the ultrasonic treatment tool 2 according to the embodiment is not provided in an area (second area) of the outer surface of the treatment portion 121, the area being where the pad 14 doesn't come into contact with.

Therefore, the pad 14 is able to be prevented from being deteriorated by the cavitation layer CL.

Furthermore, the cavitation causing portion 122 of the ultrasonic treatment tool 2 according to the embodiment is provided at the position on the outer surface of the treatment portion 121, the position other than the node position P1 of ultrasonic vibration.

That is, because the cavitation causing portion 122 is provided at the position other than the node position P1 where large stress is applied, even if the cavitation causing portion 122 is provided, the treatment portion 121 is able to have sufficient strength.

In a case where the cavitation causing portion 122 is provided by blasting, satisfactory formation of the intersecting surfaces 1221 intersecting the vibration direction of ultrasonic vibration is difficult.

By contrast, the cavitation causing portion 122 of the ultrasonic treatment tool 2 according to the embodiment is provided by laser processing.

Therefore, the intersecting surfaces 1221 intersecting the vibration direction of ultrasonic vibration are able to be formed satisfactorily.

Other Embodiments

A mode for implementing the disclosure has been described thus far, but the disclosure should not be limited only to the embodiment described above.

Ultrasonic energy and high frequency energy are adopted as types of treatment energy to be applied to a treatment target by the ultrasonic treatment tool 2 in the above described embodiment, but without being limited to this example, only ultrasonic energy may be adopted.

In the above described embodiment, the opening and closing mechanism D1 is provided in the sheath 10, but the disclosure is not limited to this example. For example, in another adoptable configuration, the jaw 11 is opened or closed relatively to the treatment portion 121 by movement of the sheath 10 itself in the distal direction Ar1 or the proximal direction Ar2. Furthermore, in another adoptable configuration for opening and closing the jaw 11, the jaw 11 may be closed relatively to the treatment portion 121 when the opening and closing mechanism D1 or the sheath 10 moves in the distal direction Ar1, or the jaw 11 may be closed relatively to the treatment portion 121 when the opening and closing mechanism D1 or the sheath 10 moves in the proximal direction Ar2.

In the above described embodiment, the ultrasonic transducer unit 5 is configured to be attachable to and detachable from the handpiece 4, but without being limited to this example, a configuration in which the handpiece 4 has the ultrasonic transducer unit 5 that has been built therein may be adopted instead.

The number of switches 8 in the above described embodiment is not necessarily two as illustrated in FIG. 1, and may be one, or three or more.

In the above described embodiment, the jaw 11 may have the reference voltage or inversely, the vibration transmission member 12 may have the reference voltage, in supplying high frequency power between the jaw 11 and the vibration transmission member 12.

First Modified Example

Figure 6:
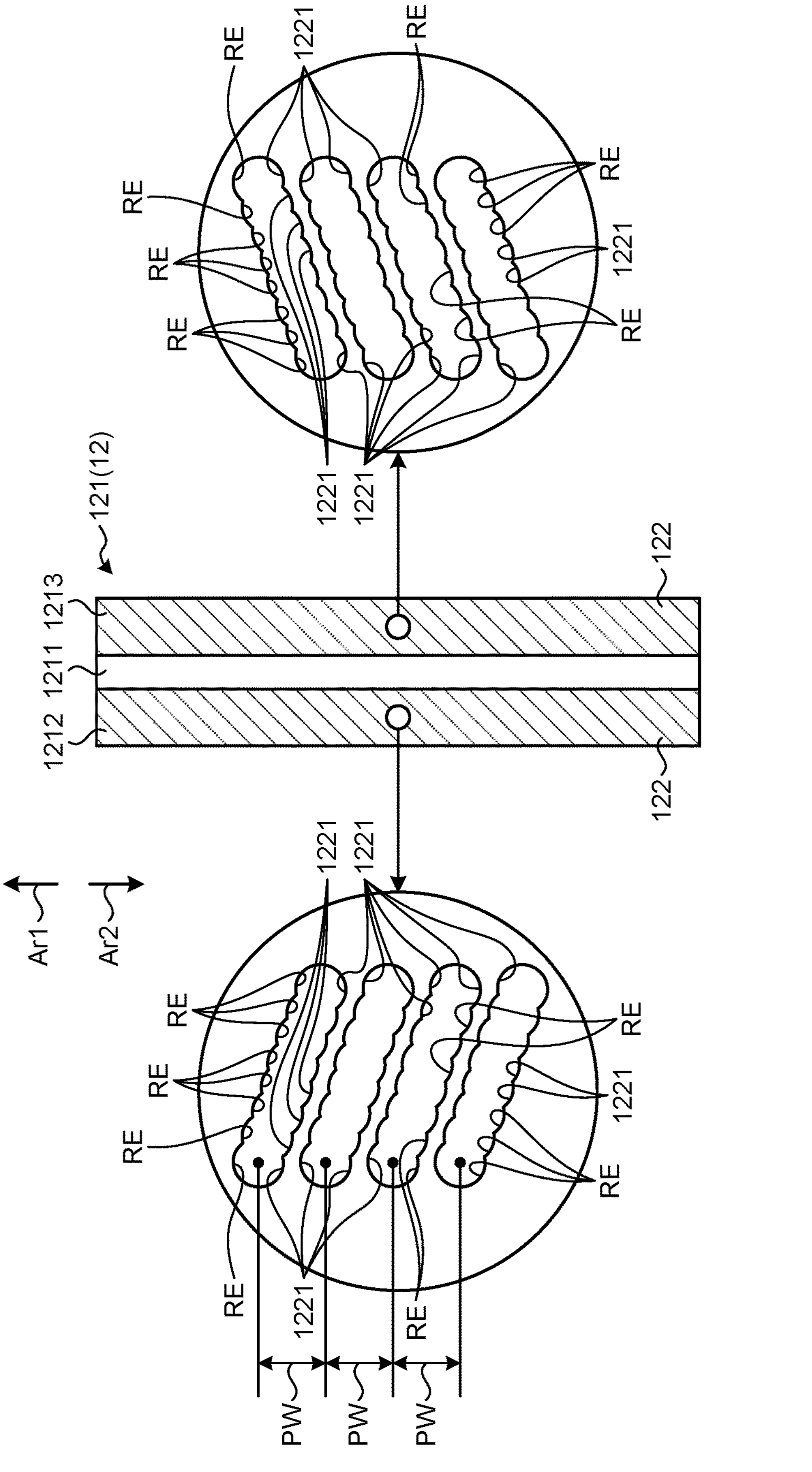
FIG. 6 is a diagram illustrating a first modified example of the embodiment.

FIG. 6 is a diagram illustrating a first modified example of the embodiment. Specifically, FIG. 6 is a diagram corresponding to FIG. 5.

In the above described embodiment, the cavitation causing portion 122 is formed by juxtaposition of the plural lines of recessed portions RE in the longitudinal direction in a state where the plural lines are parallel to each other, the recessed portions RE being lined up in the direction orthogonal to the longitudinal direction of the vibration transmission member 12, but the disclosure is not limited to this embodiment.

For example, like in the first modified example illustrated in FIG. 6, a cavitation causing portion 122 may be formed by juxtaposition of plural lines of recessed portions RE in a longitudinal direction of a vibration transmission member 12 in a state where the plural lines are parallel to each other, the recessed portions RE being lined up in a direction at a predetermined angle to a direction orthogonal to the longitudinal direction of the vibration transmission member 12. In the example of FIG. 6, the lines are inclined in a state where ends of the lines are positioned in a distal direction Ar1, the ends being distant from a first surface 1211. The cavitation causing portion 122 provided on each of a second surface 1212 and a third surface 1213 may be provided in a state of being symmetrical about the first surface 1211 when viewed from the jaw 11, as illustrated in FIG. 6.

The cavitation causing portion 122 of the first modified example may be provided in a state of satisfying at least the first condition, similarly to the embodiment described above.

In the case where the above described structure according to the first modified example is adopted also, effects similar to those of the embodiment described above are achieved.

Second Modified Example

Figure 7:
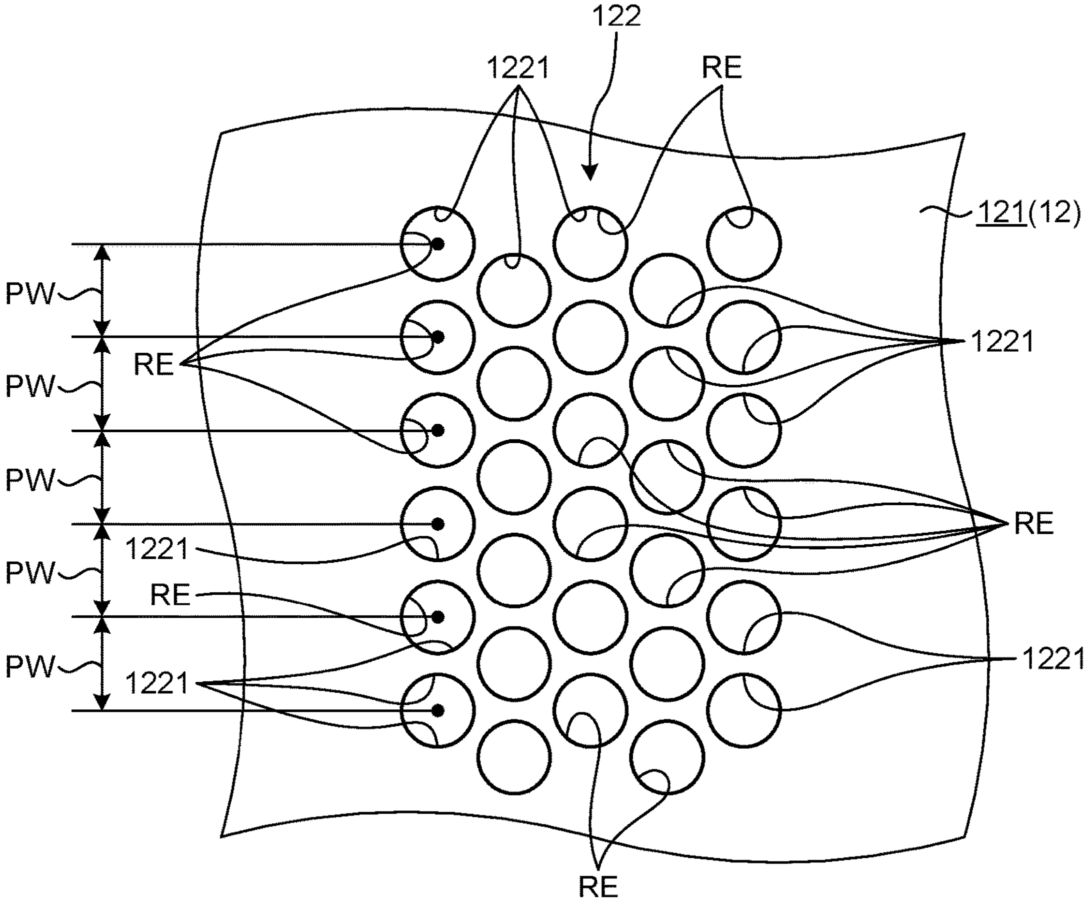
FIG. 7 is a diagram illustrating a second modified example of the embodiment.

FIG. 7 is a diagram illustrating a second modified example of the embodiment. Specifically, FIG. 7 a diagram corresponding to an enlarged diagram of FIG. 5.

The cavitation causing portion 122 in the embodiment described above may be formed by provision of the recessed portions RE in a state where all of the recessed portions RE are separate from each other, like in the second modified example illustrated in FIG. 7.

In the example of FIG. 7, plural recessed portions RE are provided at predetermined intervals and are lined up but without being limited to this example, a configuration in which the plural recessed portions RE are provided randomly may be adopted instead.

Third Modified Example

Figure 8:
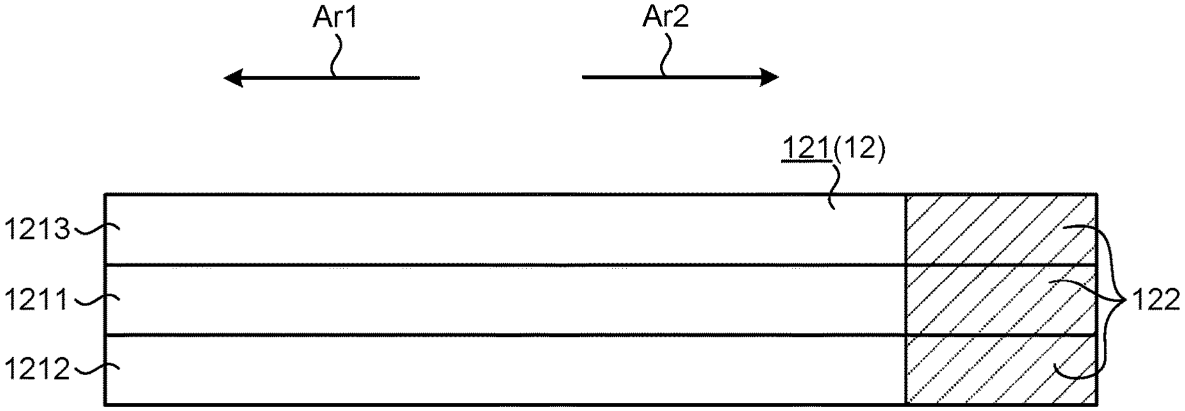
FIG. 8 is a diagram illustrating a third modified example of the embodiment.

FIG. 8 is a diagram illustrating a third modified example of the embodiment. Specifically, FIG. 8 is a diagram of a treatment portion 121 as viewed from a jaw 11. In FIG. 8, for convenience of explanation, a portion where a cavitation causing portion 122 is provided has been hatched.

The cavitation causing portion 122 in the above described embodiment is provided on the second and third surfaces 1212 and 1213, but without being limited thereto, the cavitation causing portion 122 may be provided, for example, in a part of the outer surface of the treatment portion 121, the part being lower in grasping pressure between the treatment portion 121 and the jaw 11 than other part. In the example of FIG. 8, the cavitation causing portion 122 is provided in a part of a first to third surfaces 1211 to 1213, the part of the first to third surfaces 1211 to 1213 being a part in a proximal direction Ar2, because this part in the proximal direction Ar2 is lower in grasping pressure than the other part.

The third modified example described above enables: effects similar to those of the above described embodiment to be achieved; and in addition, treatment performance to be complemented by the cavitation causing portion 122, the treatment performance being that of a part low in treatment performance (the part lower in the grasping pressure).

Fourth Modified Example

Figure 9:
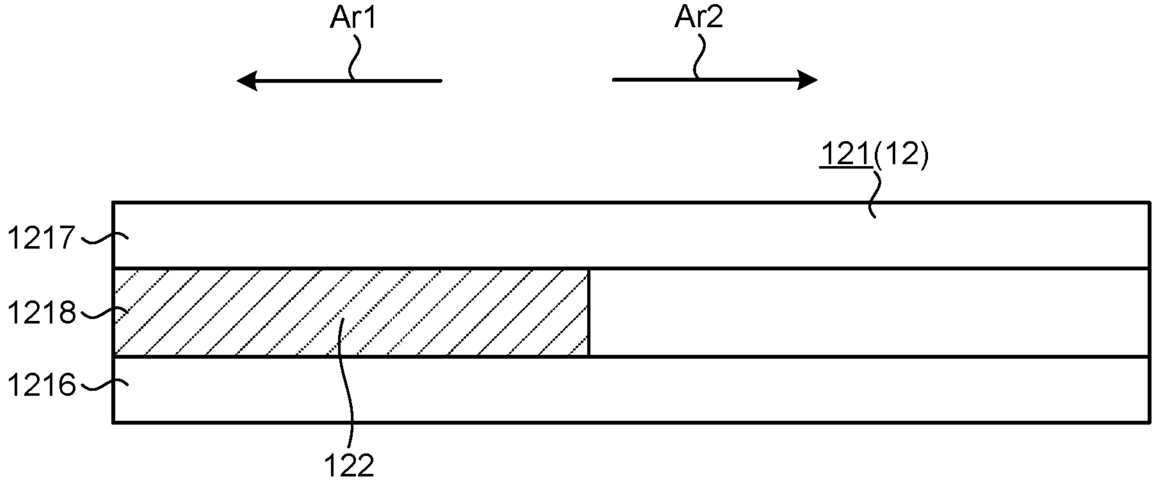
FIG. 9 is a diagram illustrating a fourth modified example of the embodiment.

FIG. 9 is a diagram illustrating a fourth modified example of the embodiment. Specifically, FIG. 9 is a diagram of a treatment portion 121 as viewed from a side distant from a jaw 11. In FIG. 9, for convenience of explanation, a portion where a cavitation causing portion 122 is provided has been hatched.

The cavitation causing portion 122 in the above described embodiment is provided on the second and third surfaces 1212 and 1213, but without being limited thereto, the cavitation causing portion 122 may be provided, for example, at least in a part of a rear surface of the outer surface of the treatment portion 121, the rear surface being distant from the jaw 11. In the example of FIG. 9, the cavitation causing portion 122 is provided only on a part of an eighth surface 1218, the part being in the distal direction Ar1.

The fourth modified example described above enables: effects similar to those of the above described embodiment to be achieved; and in addition, treatment performance to be improved when treatment is performed at the end of the treatment portion 121, the end being distant from the jaw 11.

Fifth Modified Example

As to the position where the cavitation causing portion 122 is provided, the position described with respect to the above described embodiment and the positions described with respect to the above described third and fourth modified examples may be combined as appropriate. If such combination is implemented, the cavitation causing portion 122 may not be provided on two surfaces (the fourth and fifth surfaces 1214 and 1215 in the example of FIG. 4) of the outer surface of the treatment portion 121, the two surfaces being at two ends of a width of the treatment portion 121. In the case where this configuration is adopted, for example, a blood vessel to be treated is not damaged by the surfaces at the ends of the width when the blood vessel is treated.

An ultrasonic treatment tool, a vibration transmission member, and a method of manufacturing the vibration transmission member, according to the disclosure enable stable generation of a cavitation layer in a state where the cavitation layer covers the whole cavitation causing portion.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment tool comprising:
a blade including a treatment portion, wherein the treatment portion is configured to treat a treatment target and the blade is configured to transmit an ultrasonic vibration to the treatment portion; and
a pattern on at least part of an outer surface of the treatment portion, the pattern including a plurality of protrusions, wherein each protrusion includes at least one side surface intersecting with a vibration direction of the ultrasonic vibration, the at least one side surface defining a cavitation surface,
wherein at least one cavitation surface is located within a pitch width in the vibration direction,
wherein an amplitude of the ultrasonic vibration defines the pitch width, and
wherein a height dimension of the cavitation surface is 30 μm or more and 100 μm or less.

2. The ultrasonic treatment tool according to claim 1, wherein the vibration direction of the ultrasonic vibration is a direction along a longitudinal direction of the blade,
wherein the at least one side surface comprises a plurality of intersecting sub-surfaces, and
wherein each of the plurality of intersecting sub-surfaces is oriented in a direction intersecting the longitudinal direction of the blade.

3. The ultrasonic treatment tool according to claim 2, wherein, in the direction intersecting the longitudinal direction of the blade, the plurality of intersecting sub-surfaces is connected to each other.

4. The ultrasonic treatment tool according to claim 1, further comprising:
a jaw movable relative to the treatment portion between an open position and a closed position,
wherein the jaw includes a pad,
wherein, when the jaw is in the closed position, the pad contacts a first area of the treatment portion,
wherein the pattern is in a second area of the treatment portion, and
wherein the first area of the treatment portion is different from the second area of the treatment portion.

5. The ultrasonic treatment tool according to claim 1, wherein the pattern is not located at a node position of the ultrasonic vibration.

6. The ultrasonic treatment tool according to claim 1, wherein the pattern including the plurality of protrusions extends in the vibration direction a distance that is a multiple of the pitch width.

7. The ultrasonic treatment tool according to claim 1, further comprising:
a jaw movable relative to the treatment portion between an open position and a closed position,
wherein the jaw includes a pad,
wherein, when the jaw is in the closed position, the pad contacts the treatment portion,
wherein a grasping pressure between the jaw and the part of the outer surface of the treatment portion with the pattern defines a first grasping pressure,
wherein a grasping pressure between the jaw and a second part of the outer surface of the treatment portion without the pattern defines a second grasping pressure, and
wherein the first grasping pressure is lower than the second grasping pressure.

8. The ultrasonic treatment tool according to claim 1, further comprising:
a jaw movable relative to the treatment portion between an open position and a closed position,
wherein the jaw includes a pad,
wherein, when the jaw is in the closed position, the pad contacts the treatment portion,
wherein the part of the outer surface of the treatment portion with the pattern includes at least a rear surface of the outer surface of the treatment portion, and
wherein the rear surface oriented away from the jaw.

9. The ultrasonic treatment tool according to claim 1, further comprising:
a jaw movable relative to the treatment portion between an open position and a closed position,
wherein the jaw includes a pad,
wherein, when the jaw is in the closed position, the pad contacts the treatment portion, and
wherein the part of the outer surface of the treatment portion with the pattern is other than two side surfaces of the treatment portion located at opposite ends of a width of the treatment portion, where the width is a direction orthogonal to an opening and closing direction of the jaw and a longitudinal direction of the blade.

10. The ultrasonic treatment tool according to claim 1, wherein the treatment portion is configured to flow high frequency current to the treatment target.

11. The ultrasonic treatment tool according to claim 1, wherein the cavitation surface is configured to cause cavitation by the ultrasonic vibration.

12. A blade, comprising:
a treatment portion configured to treat a treatment target, wherein the blade is configured to transmit an ultrasonic vibration to the treatment portion; and
a pattern on at least part of an outer surface of the treatment portion, the pattern including a plurality of protrusions, wherein each protrusion includes at least one side surface intersecting with a vibration direction of the ultrasonic vibration and the at least one side surface defining a cavitation surface,
wherein at least one cavitation surface is located within a pitch width in the vibration direction,
wherein an amplitude of the ultrasonic vibration defines the pitch width,
wherein the pattern including the plurality of protrusions extends in the vibration direction a distance that is a multiple of the pitch width, and
wherein a height dimension of the cavitation surface is 30 μm or more and 100 μm or less.

13. The blade according to claim 12, wherein the vibration direction of the ultrasonic vibration is a direction along a longitudinal direction of the blade,
wherein the at least one side surface comprises a plurality of intersecting sub-surfaces, and
wherein each of the plurality of intersecting sub-surfaces is oriented in a direction intersecting the longitudinal direction of the blade.

14. The ultrasonic treatment tool according to claim 13, wherein, in the direction intersecting the longitudinal direction of the blade, the plurality of intersecting sub-surfaces is connected to each other.

15. The ultrasonic treatment tool according to claim 12, wherein the cavitation surface is configured to cause cavitation by the ultrasonic vibration.

16. A method of manufacturing a blade, the method comprising:

forming by laser processing a pattern on at least part of an outer surface of a treatment portion of a blade, the pattern including a plurality of protrusions, wherein each protrusion includes at least one side surface intersecting with a vibration direction of an ultrasonic vibration transmitted along the treatment portion and the at least one side surface defining a cavitation surface, wherein at least one cavitation surface is located within a pitch width in the vibration direction, wherein an amplitude of the ultrasonic vibration defines the pitch width, wherein the pattern including the plurality of protrusions extends in the vibration direction a distance that is a multiple of the pitch width, and wherein a height dimension of the cavitation surface is 30 μm or more and 100 μm or less.

17. The method of manufacturing the blade according claim 16, wherein the laser is a short pulse laser.

* * * * *